(12) United States Patent
Okamoto et al.

(10) Patent No.: US 12,042,613 B2
(45) Date of Patent: Jul. 23, 2024

(54) BALLOON CATHETER

(71) Applicant: GOODMAN CO., LTD., Aichi (JP)

(72) Inventors: Mitsumasa Okamoto, Aichi (JP); Takashi Kunisada, Aichi (JP)

(73) Assignee: GOODMAN CO., LTD., Aichi (JP)

( * ) Notice: Subject to any disclaimer, the term of this patent is extended or adjusted under 35 U.S.C. 154(b) by 777 days.

(21) Appl. No.: 17/137,614

(22) Filed: Dec. 30, 2020

(65) Prior Publication Data

US 2021/0113820 A1    Apr. 22, 2021

Related U.S. Application Data

(63) Continuation of application No. PCT/JP2019/023088, filed on Jun. 11, 2019.

(30) Foreign Application Priority Data

Jul. 9, 2018 (JP) ................................ 2018-130087

(51) Int. Cl.
*A61M 25/10* (2013.01)

(52) U.S. Cl.
CPC ...... *A61M 25/104* (2013.01); *A61M 25/1002* (2013.01); *A61M 2025/1043* (2013.01)

(58) Field of Classification Search
CPC .. A61B 17/320725; A61B 2017/22061; A61B 2017/22051; A61M 25/10
See application file for complete search history.

(56) References Cited

U.S. PATENT DOCUMENTS

| 4,796,629 A | 1/1989 | Grayzel |
| 5,041,125 A * | 8/1991 | Montano, Jr. ..... A61M 25/1002 606/192 |

(Continued)

FOREIGN PATENT DOCUMENTS

| CN | 107206218 A | 9/2017 |
| EP | 2990069 A1 | 3/2016 |

(Continued)

OTHER PUBLICATIONS

Extended European Search Report issued in the counterpart European Patent Application No. 19833984.8, mailed Jun. 28, 2021 (7 pages).

(Continued)

*Primary Examiner* — Scott J Medway
(74) *Attorney, Agent, or Firm* — Osha Bergman Watanabe & Burton LLP (57) ABSTRACT

A balloon catheter includes an inflatable balloon disposed on a tip-end side of the balloon catheter. The balloon includes: an inflatable straight tube portion; and a tip-end side tapered portion tapered from a tip end of the straight tube portion toward the tip-end side. The balloon catheter further includes a plurality of projections that projects from an outer surface of the balloon and linearly extends along the outer surface. The plurality of projections includes: a first projection disposed at the straight tube portion; and a second projection disposed at the tip-end side tapered portion. At least a part of the second projection in a longitudinal direction thereof includes a high projecting part having a larger projection amount than a projection amount of the first projection.

5 Claims, 5 Drawing Sheets

(56) References Cited

U.S. PATENT DOCUMENTS

| | | | | |
|---|---|---|---|---|
| 5,196,024 | A * | 3/1993 | Barath | A61B 17/320725 |
| | | | | 606/191 |
| 5,254,091 | A * | 10/1993 | Aliahmad | A61M 25/1027 |
| | | | | 604/103.06 |
| 5,320,634 | A * | 6/1994 | Vigil | A61B 17/320725 |
| | | | | 604/103.08 |
| 5,458,572 | A | 10/1995 | Campbell et al. | |
| 5,624,433 | A * | 4/1997 | Radisch, Jr. | A61M 25/104 |
| | | | | 606/7 |
| 5,792,158 | A * | 8/1998 | Lary | A61B 17/320725 |
| | | | | 606/159 |
| 6,013,055 | A | 1/2000 | Bampos et al. | |
| 6,036,689 | A * | 3/2000 | Tu | A61B 18/1492 |
| | | | | 604/103.08 |
| 6,652,485 | B1 | 11/2003 | Gaudoin et al. | |
| 6,746,463 | B1 * | 6/2004 | Schwartz | A61B 17/320725 |
| | | | | 606/159 |
| 7,270,673 | B2 * | 9/2007 | Yee | A61B 17/320758 |
| | | | | 606/159 |
| 7,279,002 | B2 * | 10/2007 | Shaw | A61L 29/126 |
| | | | | 623/1.11 |
| 7,306,616 | B2 * | 12/2007 | Eidenschink | A61M 25/104 |
| | | | | 604/103.08 |
| 7,338,463 | B2 * | 3/2008 | Vigil | A61B 17/320725 |
| | | | | 604/96.01 |
| 7,708,753 | B2 * | 5/2010 | Hardert | A61M 25/104 |
| | | | | 606/128 |
| 7,771,446 | B2 * | 8/2010 | Rutter | A61M 25/104 |
| | | | | 606/191 |
| 7,771,447 | B2 * | 8/2010 | Kunis | A61B 17/320725 |
| | | | | 604/103.14 |
| 7,931,663 | B2 * | 4/2011 | Farnan | A61M 25/10 |
| | | | | 606/159 |
| 7,972,351 | B2 * | 7/2011 | Trinidad | A61M 25/1002 |
| | | | | 606/167 |
| 8,192,675 | B2 * | 6/2012 | Burton | A61B 17/320725 |
| | | | | 264/514 |
| 9,242,076 | B2 * | 1/2016 | Burton | A61M 25/10 |
| 10,166,374 | B2 * | 1/2019 | Giasolli | B65D 19/42 |
| 10,201,683 | B2 * | 2/2019 | Schneider | A61B 17/22 |
| 10,799,348 | B2 * | 10/2020 | Tilson | A61M 25/1029 |
| 2003/0144677 | A1 * | 7/2003 | Lary | A61B 17/320725 |
| | | | | 606/159 |
| 2003/0153870 | A1 * | 8/2003 | Meyer | A61M 25/104 |
| | | | | 604/96.01 |
| 2003/0229370 | A1 * | 12/2003 | Miller | A61B 17/320725 |
| | | | | 606/159 |
| 2004/0133223 | A1 * | 7/2004 | Weber | A61M 29/02 |
| | | | | 606/159 |
| 2004/0138691 | A1 * | 7/2004 | Goodin | A61M 25/104 |
| | | | | 606/194 |
| 2004/0193196 | A1 * | 9/2004 | Appling | A61B 17/320725 |
| | | | | 606/167 |
| 2005/0038383 | A1 * | 2/2005 | Kelley | A61B 17/320725 |
| | | | | 606/159 |
| 2005/0288629 | A1 * | 12/2005 | Kunis | A61M 25/10 |
| | | | | 604/22 |
| 2006/0015134 | A1 * | 1/2006 | Trinidad | A61M 25/1002 |
| | | | | 604/103.08 |
| 2006/0111736 | A1 * | 5/2006 | Kelley | A61B 17/320725 |
| | | | | 606/159 |
| 2006/0149308 | A1 * | 7/2006 | Melsheimer | A61M 25/1027 |
| | | | | 606/192 |
| 2007/0073329 | A1 * | 3/2007 | Hardert | A61M 25/104 |
| | | | | 606/192 |
| 2009/0234283 | A1 * | 9/2009 | Burton | A61M 25/1029 |
| | | | | 604/103.08 |
| 2011/0160756 | A1 | 6/2011 | Aggerholm et al. | |
| 2012/0130407 | A1 | 5/2012 | Aggerholm et al. | |
| 2015/0150586 | A1 * | 6/2015 | Aggerholm | A61M 25/0108 |
| | | | | 606/159 |
| 2015/0360007 | A1 | 12/2015 | Schneider et al. | |
| 2015/0360008 | A1 * | 12/2015 | Schneider | A61M 25/10 |
| | | | | 604/103.07 |
| 2016/0058982 | A1 * | 3/2016 | Aggerholm | A61M 25/1029 |
| | | | | 604/103.08 |
| 2016/0128718 | A1 | 5/2016 | Aggerholm et al. | |
| 2018/0043141 | A1 | 2/2018 | Sano et al. | |
| 2020/0179662 | A1 | 6/2020 | Sano et al. | |

FOREIGN PATENT DOCUMENTS

| | | |
|---|---|---|
| EP | 3115077 A1 | 1/2017 |
| EP | 3157613 A1 | 4/2017 |
| GB | 2532099 A | 5/2016 |
| JP | 2008-237844 A | 10/2008 |
| JP | 2014-506140 A | 3/2014 |
| JP | 2015-104671 A | 6/2015 |
| JP | 2016-52452 A | 4/2016 |
| JP | 2017-522078 A | 8/2017 |
| WO | 2015195757 A1 | 12/2015 |

OTHER PUBLICATIONS

Office Action issued in corresponding Korean Patent Application No. 10-2020-7037568 dated Oct. 31, 2022 (9 pages).
Office Action issued in related Korean Patent Application No. 10-2020-7037569 dated Oct. 31, 2022 (10 pages).
Final Office Action issued in related U.S. Appl. No. 17/137,638 dated Nov. 8, 2022 (6 pages).
Office Action issued in related Chinese Patent Application No. 201980035516.0 dated May 26, 2023 (12 pages).
Office Action issued in related Indian Patent Application No. 202017055896 dated Sep. 16, 2021 (5 pages).
Office Action issued in related Indian Patent Application No. 202017055895 dated Sep. 24, 2021 (5 pages).
Office Action issued in related U.S. Appl. No. 17/137,638 dated Feb. 2, 2022 (14 pages).
Office Action issued in related U.S. Appl. No. 17/137,638 dated Jun. 22, 2022 (8 pages).
International Preliminary Report on Patentability issued for PCT/JP2019/023089, mailed Jan. 21, 2021 (13 pages).
International Preliminary Report on Patentability issued for PCT/JP2019/023088, mailed Jan. 21, 2021 (11 pages).
International Search Report issued in corresponding International Application No. PCT/JP2019/023088 mailed Jul. 23, 2019 (4 pages).
International Search Report issued in corresponding International Application No. PCT/JP2019/023089 mailed Jul. 23, 2019 (4 pages).
Office Action issued in related Chinese Patent Application No. 201980035521.1 dated Dec. 24, 2021 (14 pages).
Office Action issued in related Chinese Patent Application No. 201980035516.0 dated Dec. 24, 2021 (14 pages).
Rejection Decision issued in corresponding Chinese Application No. 201980035521.1; dated Jan. 5, 2023 (12 pages).
Office Action issued in corresponding Chinese Application No. 201980035516.0; dated Nov. 25, 2022 (13 pages).
Advisory Action issued in corresponding U.S. Appl. No. 17/137,638; dated Jan. 23, 2023 (8 pages).
Office Action issued in related European Patent Application No. 19834109.1 dated Apr. 5, 2023 (6 pages).
Office Action issued in corresponding Japanese Patent Application No. 2020-530043, mailed on Aug. 17, 2021 (7 pages).
Office Action issued in corresponding Japanese Patent Application No. 2020-530044, mailed on Aug. 17, 2021 (7 pages).
Office Action issued in related Chinese Patent Application No. 201980035521.1 dated Jul. 25, 2022 (13 pages).
Office Action issued in related Chinese Patent Application No. 201980035516.0 dated Jul. 14, 2022 (14 pages).
Office Action issued in related Japanese Patent Application No. 2020-530044, mailed on Aug. 17, 2021 (7 pages).

* cited by examiner

BALLOON CATHETER

CROSS-REFERENCE TO RELATED APPLICATION

The present application is a continuation of PCT International Application No. PCT/JP2019/023088 filed on Jun. 11, 2019 which claims the benefit of priority from Japanese Patent Application No. 2018-130087 filed on Jul. 9, 2018, the entire contents of which are incorporated herein by reference.

BACKGROUND

Technical Field

The present invention relates to balloon catheter.

Description of the Related Art

A balloon catheter has been used for remedies such as PTA (percutaneous transluminal angioplasty) and PTCA (percutaneous transluminal coronary angioplasty), etc. The balloon catheter includes an inflatable (i.e., inflatable and deflatable) balloon on a tip-end side thereof. As for the balloon catheter, the balloon in a deflated state is introduced into a spot narrowed or obstructed by a lesion or the like generated in a blood vessel and then the spot is stretched by inflating the balloon. The balloon also includes a straight tube region having a diameter maximized during inflation and a pair of cone regions provided on a base-end side and a tip-end side of the straight tube region and reduced in diameter toward a side away from the straight tube region.

In this connection, in a case where a lesion in a blood vessel is hardened due to calcification or the like, the lesion using the balloon would be difficult to stretch. Accordingly, Patent Literature 1 proposes, as a countermeasure against such a case, a technology where a linear element is projectingly provided on an outer surface of the balloon. This element extends in an axial direction across the straight tube region and the cone regions of the balloon. The configuration of Patent Literature 1 enables making a cut (crack) in the lesion with the element by inflating the balloon, so that the lesion can be broken with the cut serving as a trigger. Therefore, even in a case where the lesion is hardened, it is possible to stretch the lesion.

It should be noted that according to the technology of Patent Literature 1 described above, a projection height of the element from the outer surface of the balloon is lower at each of the cone regions than at the straight tube region.

PATENT LITERATURE

Patent Literature 1: Japanese Patent Laid-Open No. 2014-506140

Meanwhile, in a case where a hard lesion generated in a blood vessel (blood vessel wall) is large, it is assumed that a balloon cannot be introduced inside a spot narrowed by the lesion (in other words, the inside of the lesion) well. For example, it is assumed that a straight tube region of the balloon cannot be positioned inside the lesion. Accordingly, in such a case, it is likely that only a cone region in a tapered shape on a tip-end side of the balloon (hereinafter, referred to as a tip-end cone region) is first introduced inside the lesion and the balloon is inflated. It is then likely that only a proximal side of the lesion is first stretched due to the inflation.

In this connection, in inflating the balloon with only the tip-end cone region introduced into the lesion as described above, it is likely that, in a case where the balloon catheter of Patent Literature 1 described above is used, the balloon is inflated while making a cut in the lesion with the element provided at the tip-end cone region. However, in the balloon catheter of Patent Literature 1 described above, the element has a low projection height at the tip-end cone region and thus a cut would fail to be made well in the lesion with the element. Therefore, the lesion is likely to be difficult to favorably break.

SUMMARY

One or more embodiments of the present invention provide a balloon catheter configured to, in a case where a lesion generated in the body is large, favorably break the lesion.

A balloon catheter of one or more embodiments includes: an inflatable and deflatable balloon on a tip-end side, the balloon including a straight tube portion having a diameter maximized during inflation and a tip-end tapered portion (i.e., tip-end side tapered portion) reduced in diameter from a tip-end portion (i.e., tip end) of the straight tube portion toward the tip-end side; and a projection projectingly provided on an outer surface of the balloon and linearly extending along the outer surface, the projection including a first projection provided at the straight tube portion and a second projection provided at the tip-end tapered portion, in which at least a part of the second projection in a longitudinal direction is a high projection (i.e., high projecting part) having a larger projection amount from the outer surface than the first projection.

According to one or more embodiments, the linear projection projectingly provided on the outer surface of the balloon includes the first projection provided at the straight tube portion and the second projection provided at the tip-end tapered portion. In this case, at least a part of the second projection in the longitudinal direction is a high projection having a larger projection amount from the outer surface of the balloon than the first projection. In a case where a lesion generated in the body (for example, in a blood vessel) is large, such a configuration makes it possible to, in inflating the balloon with the tip-end tapered portion in a tapered shape introduced inside the lesion, easily make a cut in the lesion with the second projection (high projection). Thus, even in the case where the lesion is large, the lesion can be favorably broken with the cut serving as a trigger.

In a balloon catheter of one or more embodiments, the high projection has a larger width than the first projection.

According to one or more embodiments, the high projection, which has the larger projection amount, has a larger width than the first projection. This makes it possible to keep the high projection from leaning in making a cut in a lesion with the high projection, so that a cut can be more easily made in the lesion.

In a balloon catheter of one or more embodiments, the second projection extends in an axial direction of the balloon along an outer surface of the tip-end tapered portion, and the projection amount of the second projection is increased from a base-end side toward a tip-end side thereof, whereby at least the tip-end side is the high projection.

According to one or more embodiments, the second projection extends in the axial direction of the balloon along the outer surface of the tip-end tapered portion. Further, the projection amount of the second projection is increased from the base-end side toward the tip-end side thereof, whereby at least the tip-end side serves as the high projection. In this connection, in a case where a lesion generated in the body is large, it is assumed that only the tip-end side of the tip-end tapered portion can be inserted inside the lesion. In this regard, even in such a case, the above-described configuration enables the lesion to be favorably broken with the high projection provided on the tip-end side of the tip-end tapered portion.

In a balloon catheter of one or more embodiments, the projection amount of the second projection is continuously increased from the base-end side toward the tip-end side thereof.

According to one or more embodiments, with the projection amount of the second projection continuously increased from the base-end side toward the tip-end side, a projection end portion of the second projection can be kept from being cornered. Thus, the effect of the above-described embodiments can be achieved while keeping canal walls, etc. in the body from being damaged by the second projection.

In a balloon catheter of one or more embodiments, a width of the second projection is increased from the base-end side toward the tip-end side thereof In making a cut in a lesion with the second projection, it is supposed that a portion with a larger projection amount is more likely to lean. In this regard, according to one or more embodiments, in the configuration where the projection amount of the second projection is increased from the base-end side toward the tip-end side, the width of the second projection is increased from the base-end side toward the tip-end side. In this case, in making a cut in a lesion with the second projection, the second projection can be favorably kept from leaning therethroughout in the longitudinal direction.

Alternatively, it is possible that the second projection is kept from leaning by increasing the width of the second projection therethroughout in the longitudinal direction. This case, however, entails a disadvantage such as a decrease in flexibility of the balloon. In this regard, the above-described configuration can achieve the above-described effects while avoiding such a disadvantage.

BRIEF DESCRIPTION OF DRAWINGS

The above-described features and advantages of one or more embodiments of the present invention will be further clarified by the following detailed description made with reference to the attached drawings.

DETAILED DESCRIPTION

Figure 1:
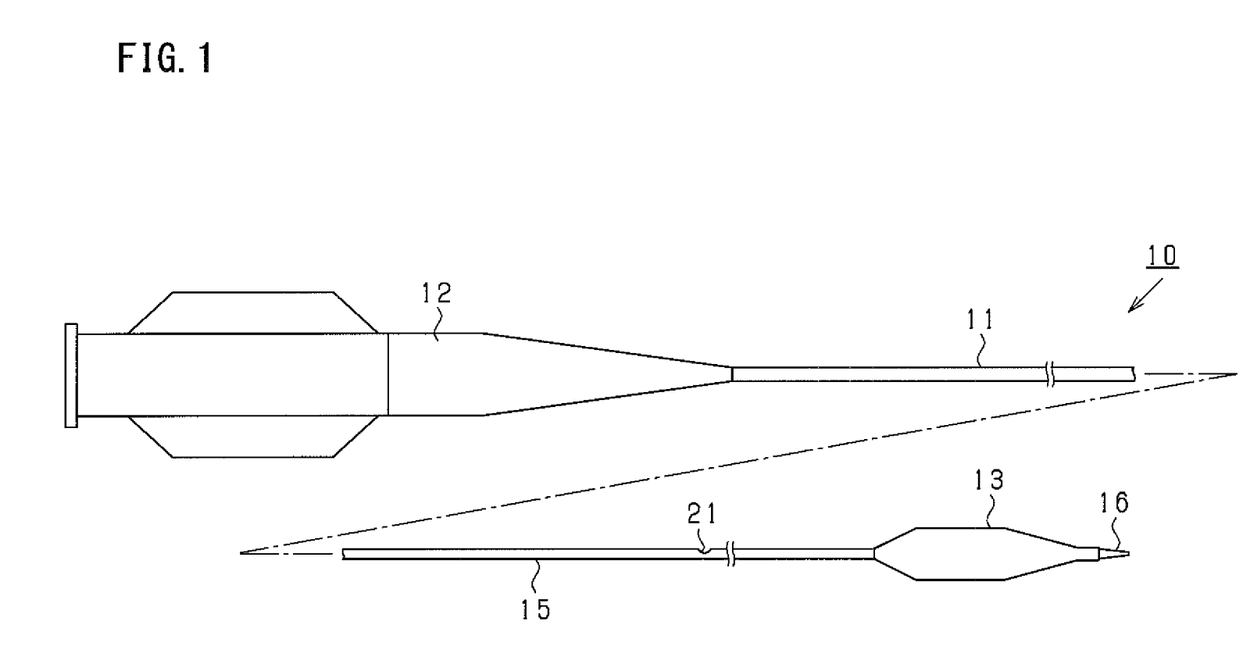
FIG. 1 is a schematic overall side view showing a configuration of a balloon catheter.

Description will be made below on embodiments of a balloon catheter on the basis of the drawings. First, an overall configuration of a balloon catheter 10 will be described with reference to FIG. 1. FIG. 1 is a schematic overall side view showing a configuration of the balloon catheter 10.

As shown in FIG. 1, the balloon catheter 10 includes a catheter body 11, a hub 12 attached to a base-end portion (proximal-end portion) of the catheter body 11, and a balloon 13 attached to a tip-end side (distal-end side) of the catheter body 11.

The catheter body 11 includes an outer tube 15 and an inner tube 16 inserted in the outer tube 15. The outer tube 15 is formed of a resin material; for example, it is formed of polyamide elastomer. A base-end portion of the outer tube 15 is bonded to the hub 12, while a tip-end portion thereof is bonded to the balloon 13. Further, the outer tube 15 has therein a lumen 15a (see FIG. 2) extending therethroughout in an axial direction thereof. The lumen 15a is in communication with the inside of the hub 12 while being in communication with the inside of the balloon 13.

It should be noted that the outer tube 15 may be formed by bonding a plurality of tubes aligned in the axial direction to each other. In this case, it is likely that, for example, one of the tubes on a base-end side is formed of a metal material such as a Ni—Ti alloy or stainless steel, while one on a tip-end side is formed of a resin material such as polyamide elastomer.

The inner tube 16 is formed of a resin material; for example, it is made of polyamide elastomer. The inner tube has therein a lumen 16a (see FIG. 2) extending therethroughout in an axial direction thereof. A base-end portion of the inner tube 16 is bonded at an axial middle position of the outer tube 15, while a part of a tip-end side thereof is extended on a tip-end side relative to the outer tube 15. Further, the balloon 13 is provided on the inner tube 16, externally covering such an extended region.

The lumen 15a of the outer tube 15 functions as a fluid lumen where a compressed fluid is to flow in inflating or deflating the balloon 13. Meanwhile, the lumen 16a of the inner tube 16 functions as a guide wire lumen where a guide wire G is to be inserted. A base-end opening 21 of the lumen 16a is present at an axial middle position of the balloon catheter 10. The present balloon catheter 10 is thus in the form of a so-called RX catheter. It should be noted that the base-end opening 21 of the lumen 16a may be included in a base-end portion of the balloon catheter 10. In this case, the balloon catheter 10 is in the form of a so-called over-the-wire catheter.

Figure 2:
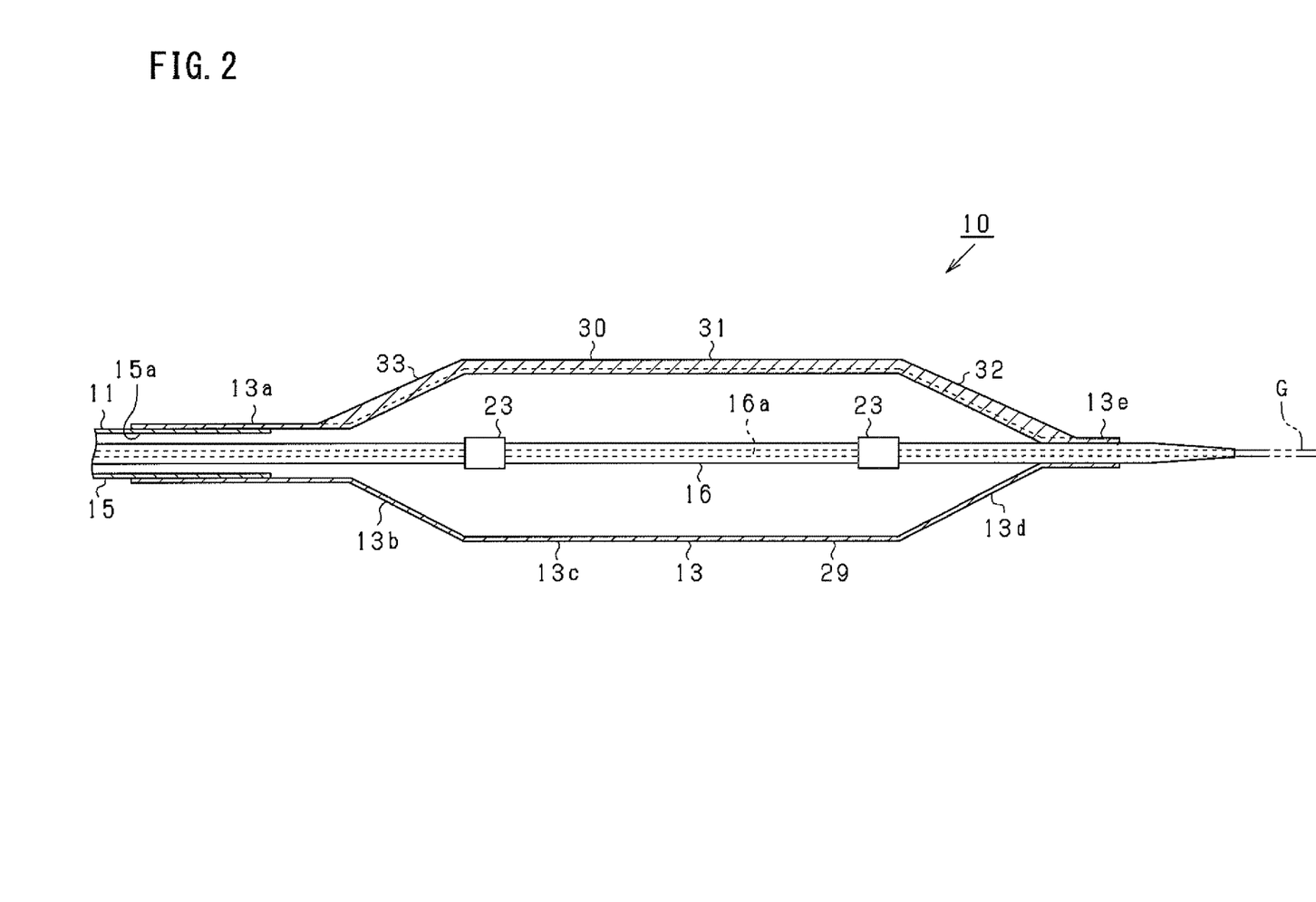
FIG. 2 is a side view of a balloon in an inflated state and a vicinity thereof, showing the balloon and an outer tube in a longitudinal cross section.
Figure 3A:
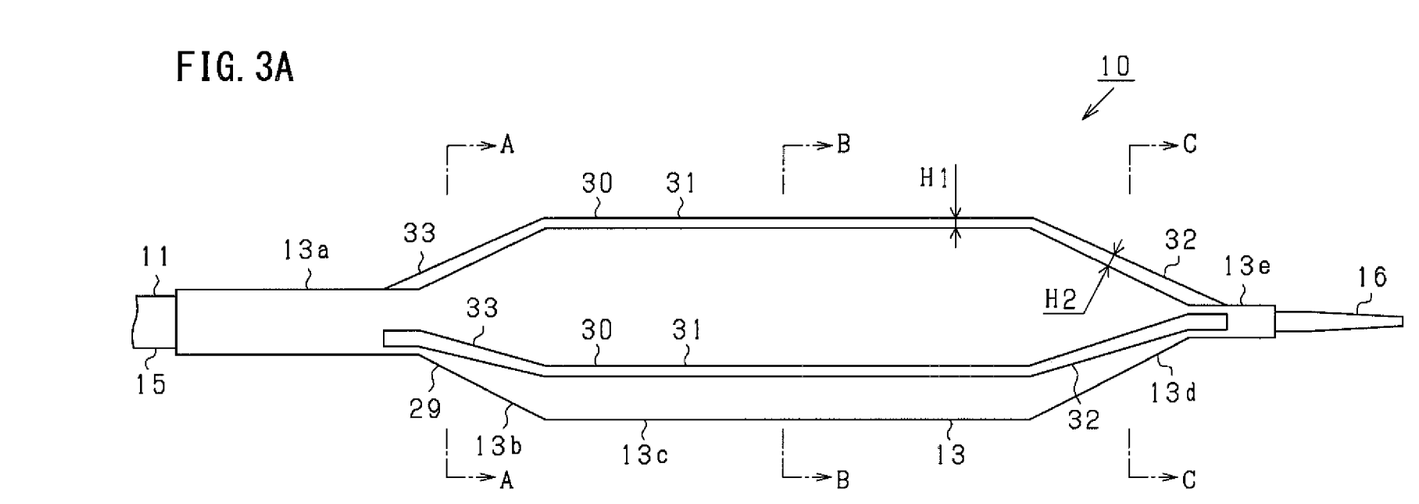
FIG. 3A is a side view showing a configuration of the balloon in the inflated state and the vicinity thereof.
Figure 3B:
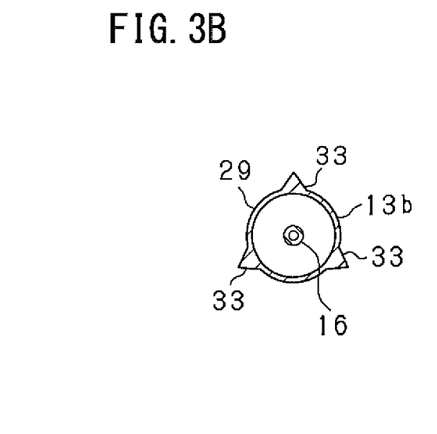
FIG. 3B is a cross sectional view taken along an A-A line in FIG. 3A.
Figure 3C:
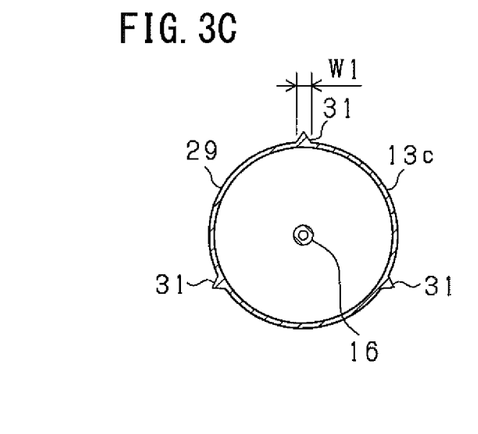
FIG. 3C is a cross-sectional view taken along a B-B line in FIG. 3A.
Figure 3D:
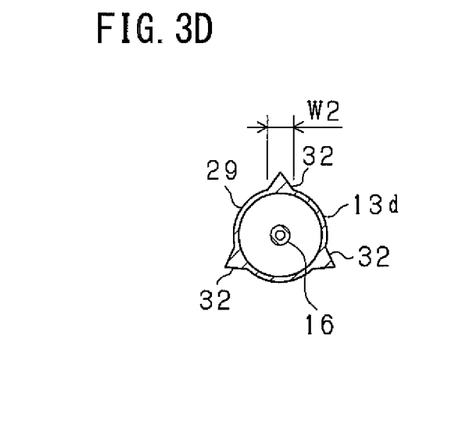
FIG. 3D is a cross sectional view taken along a C-C line in FIG. 3A.
Figure 4A:
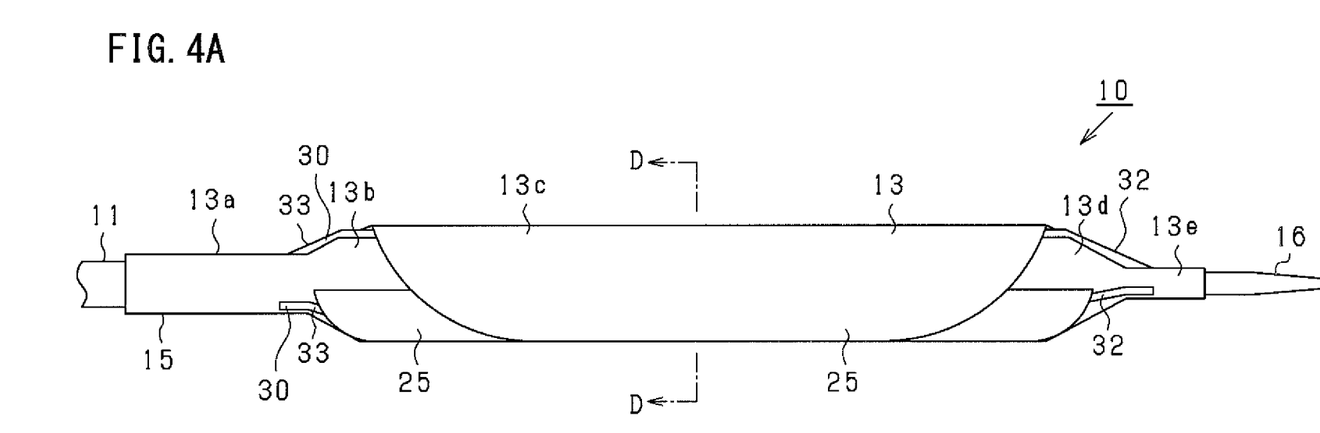
FIG. 4A is a side view showing a configuration of the balloon in a deflated state and the vicinity thereof and FIG. 4B is a cross sectional view taken along a D-D line in FIG. 4A.
Figure 4B:
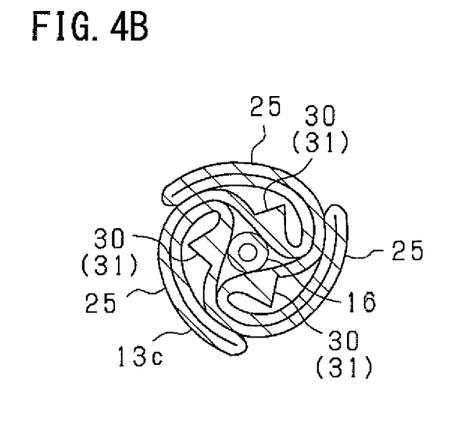

Next, a configuration of the balloon 13 and a vicinity thereof will be described on the basis of FIG. 2 to FIG. 4. FIG. 2 is a side view of the balloon 13 in an inflated state and the vicinity thereof, showing the balloon 13 and the outer tube 15 in a longitudinal cross section. FIG. 3A is a side view showing a configuration of the balloon 13 in the inflated state and the vicinity thereof, FIG. 3B is a cross sectional view taken along an A-A line in FIG. 3A, FIG. 3C is a cross-sectional view taken along a B-B line in FIG. 3A, and FIG. 3D is a cross sectional view taken along a C-C line in FIG. 3A. FIG. 4A is a side view showing a configuration of the balloon 13 in a deflated state and the vicinity thereof and FIG. 4B is a cross sectional view taken along a D-D line in FIG. 4A.

As described above, the balloon 13 is provided on the inner tube 16, externally covering the extended region extended on the tip-end side relative to the outer tube 15. As shown in FIG. 2 and FIG. 3(a), a base-end portion of the balloon 13 is bonded to the tip-end portion of the outer tube 15, while a tip-end portion thereof is bonded to the tip-end side of the inner tube 16.

The balloon 13 is made of a thermoplastic polyamide elastomer. However, the balloon 13 may be formed of any other thermoplastic resin instead of polyamide elastomer as long as the balloon 13 can be favorably inflated and deflated with the supply and discharge of the fluid. For example, it may be formed of polyethylene, polyethylene terephthalate, polypropylene, polyurethane, polyamide, polyimide, polyimide elastomer, silicone rubber, or the like.

The balloon 13 is formed of a film 29 with a predetermined thickness. The balloon 13 includes opposite bonded portions bonded to the catheter body 11 and an inflation/deflation portion provided between the bonded portions and that is to be inflated and deflated. Specifically, the balloon 13 includes: a base-end leg region 13a bonded to the tip-end portion of the outer tube 15; a base-end cone region 13b tapered such that the inner diameter and outer diameter of the balloon 13 are continuously increased toward the tip-end side; a straight tube region 13c having the same inner diameter and outer diameter therethroughout in a length direction and defining a maximum outer diameter region of the balloon 13; a tip-end cone region 13d tapered such that the inner diameter and outer diameter of the balloon 13 are continuously reduced toward the tip-end side; and a tip-end leg region 13e bonded to the tip-end side of the inner tube 16 in this order from the base-end side. In this case, the base-end cone region 13b, the straight tube region 13c, and the tip-end cone region 13d constitute the inflation/deflation portion, while the base-end leg region 13a and the tip-end leg region 13e each constitute the bonded portion.

It should be noted that the straight tube region 13c corresponds to a "straight tube portion" and the tip-end cone region 13d corresponds to a "tip-end tapered portion".

The balloon 13 is brought into the inflated state when the compressed fluid is supplied into the balloon 13 through the lumen 15a of the outer tube 15 and brought into the deflated state when a negative pressure is applied to the lumen 15a to cause the compressed fluid to be discharged out of the balloon 13. As shown in FIGS. 4A and 4B, the balloon 13 includes a plurality of (in the present embodiment, three) wings 25 formed in the deflated state. These wings 25 are provided at predetermined intervals (in particular, regular intervals) in a circumferential direction of the balloon 13. The wings 25 are formed to extend in the axial direction at the inflation/deflation portion of the balloon 13. In this case, the wings 25 extend across the base-end cone region 13b, the straight tube region 13c, and the tip-end cone region 13d. With the balloon 13 being in the deflated state, these wings 25 are folded in the circumferential direction of the balloon 13, being wrapped around the inner tube 16.

It should be noted that a pair of contrast rings 23 are attached to the inner tube 16 inside the balloon 13. The contrast rings 23 are intended to improve the visibility of the balloon 13 during x-ray projection so that the balloon 13 is easily positioned with respect to a targeted treatment spot.

In this connection, in the present balloon catheter 10, an outer surface of the balloon 13 is provided with a linear projection (hereinafter, referred to as a linear projection 30) extending along an axial direction of the balloon 13. In inflating the balloon 13 to stretch a lesion, the linear projection 30 is intended to make a cut in the lesion. Even in a case where the lesion is hardened due to calcification or the like, the present balloon catheter 10 makes a cut in the lesion by virtue of the linear projection 30, so that the lesion can be broken with the cut serving as a trigger. The present balloon catheter 10 is thus configured as a so-called cutting balloon catheter (also referred to as a scoring balloon catheter).

A detailed description will be made below on a configuration related to the linear projection 30. As shown in FIG. 2 and FIG. 3A, the linear projection 30 continuously extends in the axial direction of the balloon from the base-end leg region 13a to the tip-end leg region 13e. Thus, the linear projection 30 extends throughout each of the base-end cone region 13b, the straight tube region 13c, and the tip-end cone region 13d of the balloon 13 with respect to the axial direction. A plurality of such linear projections 30 are provided in the circumferential direction of the balloon 13 at predetermined intervals (in particular, regular intervals); in the present embodiment, three linear projections 30 are provided. These linear projections 30 are each integrated with the balloon 13. Further, in the present embodiment, these linear projections 30 are the same in configuration.

The linear projections 30 each have, therethroughout in a longitudinal direction thereof, a transverse cross section (in particular, a cross section perpendicular to the longitudinal direction) in a triangular shape (the same shape). The linear projections 30 are each provided in an orientation where one of the corners thereof projects toward an outer circumferential side (radially outside) of the balloon 13. It should be noted that the linear projections 30 are each not necessarily in a triangular shape in a transverse cross section but may be in any other shape, such as a semicircular shape or a rectangular shape, in a transverse cross section.

The linear projections 30 each include a first projection 31 provided at the straight tube region 13c, a second projection 32 provided at the tip-end cone region 13d, and a third projection 33 provided at the base-end cone region 13b. The first projection 31 has a constant projection height H1 (projection amount) from the outer surface of the balloon 13 therethroughout in the longitudinal direction. The first projection 31 also has a constant width W1 (see FIG. 3C) therethroughout in the longitudinal direction. It should be noted that the width W1 of the first projection 31 refers to a length in a direction perpendicular to each of the longitudinal direction and projecting direction of the first projection 31.

A projection height H2 (projection amount) of the second projection 32 from the outer surface of the balloon is larger than the projection height H1 of the first projection 31. In particular, the second projection 32 has the projection height H2 larger than the projection height H1 of the first projection 31 therethroughout in the longitudinal direction. Thus, the whole of the second projection 32 corresponds to a "high projection" in the present embodiment. Further, the projection height H2 of the second projection 32 is increased from a base-end side (a straight tube region 13c side) toward a tip-end side (a tip-end leg region 13e side). In particular, the projection height H2 of the second projection 32 is continuously increased throughout the second projection 32 from the base-end side toward the tip-end side.

A width W2 (see FIG. 3D) of the second projection 32 is larger than the width W1 of the first projection 31. In particular, the second projection 32 has the width W2 larger than the width W1 of the first projection 31 therethroughout in the longitudinal direction. Further, the width W2 of the second projection 32 is increased from the base-end side toward the tip-end side. In particular, the width W2 of the second projection 32 is continuously increased throughout the second projection 32 from the base-end side toward the tip-end side. It should be noted that the width W2 of the second projection 32 refers to a length in a direction perpendicular to each of the longitudinal direction and projecting direction of the second projection 32.

The third projection 33 has, therethroughout in the longitudinal direction, a projection height (projection amount) from the outer surface of the balloon 13 larger than the projection height H1 of the first projection 31, and the projection height is continuously increased from the tip-end side (the straight tube region 13c side) toward the base-end side (the base-end leg region 13a side). Further, the third projection 33 has a width larger than the width W1 of the first projection 31 therethroughout in the longitudinal direction, and the width is continuously increased from the tip-end side toward the base-end side.

In the deflated state of the balloon 13, the plurality of wings 25 are formed at the inflation/deflation portion (the straight tube region 13c and the cone regions 13b and 13d) of the balloon 13 and these wings 25 are folded in the circumferential direction of the balloon 13 as described above. In this case, as shown in FIGS. 4A and 4B, the linear projections 30 of the balloon 13, which are in a one-to-one relationship with the wings 25, are provided on the inside of the folded respective wings 25. This causes the linear projections 30 (in particular, the majority thereof) to be externally covered by the wings 25 in the deflated state of the balloon 13.

Next, a brief description will be made on a manufacturing method of manufacturing the balloon 13.

First, a tubular parison, which is to be made into the balloon 13, is produced by extrusion molding. The tubular parison, which is formed in the shape of a circular tube, has an outer circumferential surface provided with a protruding stripe extending in the axial direction. A plurality of (specifically, three) such protruding stripes, each of which has a triangular transverse cross section, are formed at regular intervals in a circumferential direction of the tubular parison.

Subsequently, the tubular parison is stretched in a length direction and then blow-molded under predetermined conditions using a mold with a cavity corresponding to the shape of the balloon 13. Grooves for accommodating the protruding stripes are formed in the mold, and the tubular parison is set in the cavity with the protruding stripes accommodated in these grooves. The blow-molding is then performed in such a set state. During the blow-molding, the tubular parison is heated to expand within the mold (cavity). As a result of the blow-molding, the tubular parison is biaxially stretched while the protruding stripes are formed as the linear projections 30. Then, both ends of the stretched tubular parison are cut, thus completing the manufacturing of the balloon 13.

The above is the description of the manufacturing method of the balloon 13. It should be noted that the manufacturing method of the balloon 13 is not necessarily limited to the above-described method but another manufacturing method may be employed.

Next, description will be made on a method of using the balloon catheter 10. Here, description will be made on a process for stretching a lesion generated in a blood vessel using the balloon catheter 10. It should be noted that FIGS. 5A-5E are diagrams of assistance in explaining such a process.

First, a guiding catheter is inserted through a sheath introducer inserted in a blood vessel and a tip-end opening of the guiding catheter is introduced into a coronary ostium. Next, the guide wire G is inserted through the guiding catheter and the inserted guide wire G is introduced from the coronary ostium to a peripheral site via the lesion.

Subsequently, the balloon catheter 10 is introduced into the guiding catheter along the guide wire G. After the introduction, the balloon 13 is introduced (positioned) toward a lesion 35 while a push/pull operation is performed. It should be noted that the balloon 13 is in the deflated state during this introduction.

Figure 5A:
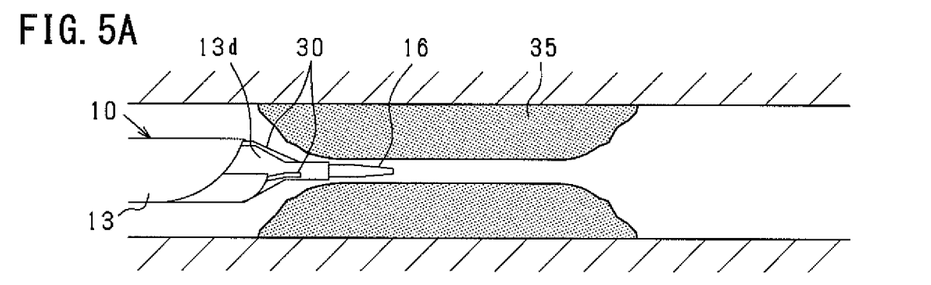
FIGS. 5A-5E are diagrams of assistance in explaining a method of using the balloon catheter.

In this connection, in an example of FIG. 5A, the lesion 35 generated in the blood vessel is relatively large. Further, the lesion 35 is hardened due to calcification. In this case, a spot narrowed by the lesion 35, i.e., an inner region of the lesion 35, is considerably narrowed, so that it is assumed that the balloon 13 cannot be introduced (positioned) inside the lesion 35 well. For example, it is assumed that the straight tube region 13c of the balloon 13 fails to be introduced inside the lesion 35.

Figure 5B:
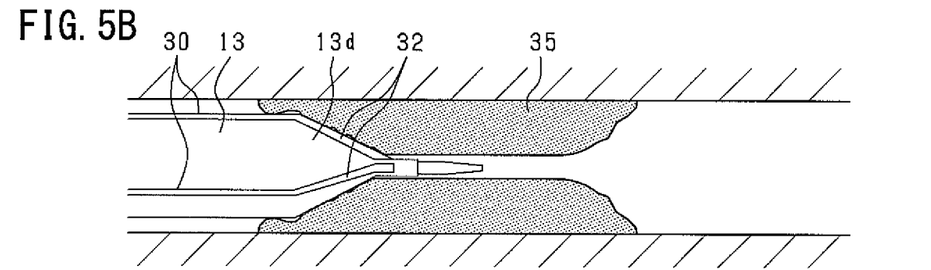

Accordingly, in such a case, only the tip-end cone region 13d, which is in a tapered shape, of the balloon 13 is first introduced inside the lesion 35 as shown in FIG. 5A. The balloon 13 is then inflated in such an introduced state. This causes the second projections 32 of the tip-end cone region 13d to be pressed against the lesion 35 as shown in FIG. 5B, making a cut (crack) in the lesion 35 with the second projections 32.

In this connection, the second projections 32 each have the projection height H2 larger than the projection height H1 of each first projection 31 of the straight tube region 13c, so that a cut can be made in the lesion 35 well with the second projections 32. Consequently, the lesion can be favorably broken with the cut serving as a trigger. Then, as a result of the breakage of the lesion 35, the lesion 35 can be stretched outward.

Figure 5C:
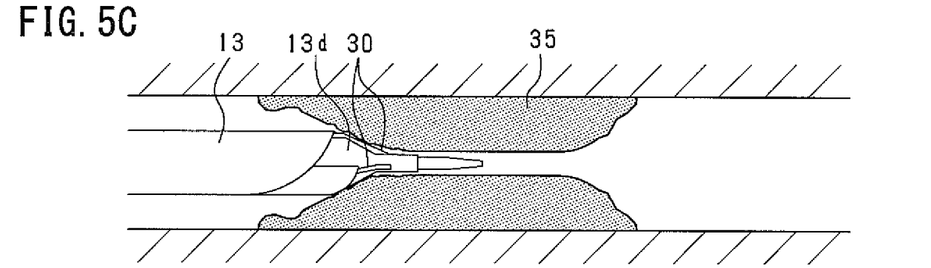

Subsequently, as shown in FIG. 5C, the balloon 13 is deflated. The balloon 13 in the deflated state is then moved further toward the distal side (tip-end side), and the tip-end cone region 13d of the balloon 13 is introduced inside a non-stretched portion, which has not been stretched yet, of the lesion 35. At this time, the straight tube region 13c of the balloon 13 is positioned inside a cone-stretched portion, which has already been stretched by the tip-end cone region 13d, of the lesion 35. The balloon 13 is then inflated again in such an introduced state of the balloon 13.

Figure 5D:
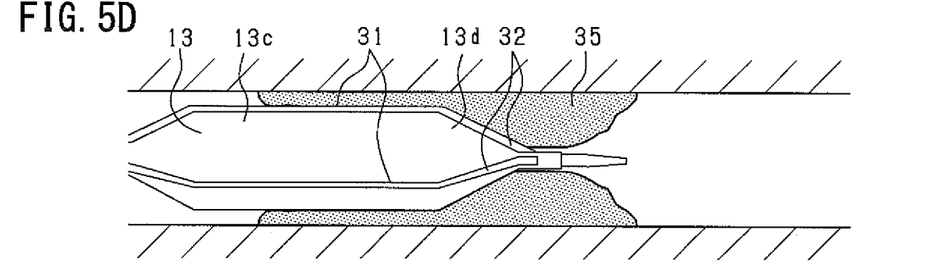

As a result of the inflation of the balloon 13, the non-stretched portion of the lesion 35 is broken with the second projections 32 of the tip-end cone region 13d in a similar manner as described above, and the non-stretched portion is stretched due to the breakage (see FIG. 5D). Further, the cone-stretched portion of the lesion 35 is stretched further outward by the straight tube region 13c. In particular, the cone-stretched portion of the lesion 35 is broken with the first projections 31 of the straight tube region 13c, and the cone-stretched portion is stretched further outward due to the breakage.

Figure 5E:
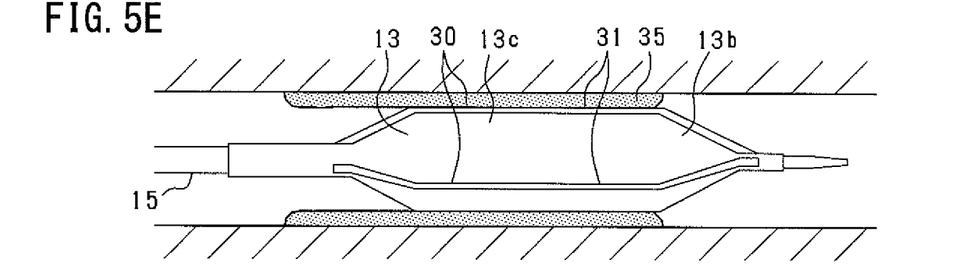

Such a process causes the non-stretched portion (and the cone-stretched portion) of the lesion 35 to be stretched sequentially from the proximal side toward the distal side. The whole of the lesion 35 is then eventually stretched by the balloon 13 as shown in FIG. 5E.

After the lesion 35 is stretched, for example, an operation for deflating the balloon 13 and pulling the balloon catheter 10 out of the body is performed. A series of operations are thus completed.

It should be noted that while the balloon catheter 10 is introduced through a blood vessel and mainly used for the treatment of the blood vessel such as a coronary artery, a femoral artery, or a pulmonary artery as described above, the balloon catheter 10 is also usable for any other "vessel", such as a ureter and a gastrointestinal tract, in addition to a blood vessel and a "body cavity" in a living body.

The configuration of the present embodiment described above in detail achieves the following excellent effects.

Each of the second projections 32 (corresponding to a high projection), which has a larger projection height than each of the first projections 31, has the width W2 larger than the width W1 of the first projection 31. This makes it possible to keep the second projection 32 from leaning in making a cut in a lesion with the second projection 32, so that a cut can be more easily made in the lesion.

The projection height H2 of the second projection 32 is increased from the base-end side toward the tip-end side. In this connection, for example, in a case where a lesion generated in the body is considerably large, it is assumed that only the tip-end side of the tip-end cone region 13d can be inserted inside the lesion. In this regard, in such a case, the above-described configuration enables the lesion to be favorably broken with the second projection 32 provided on the tip-end side of the tip-end cone region 13d, i.e., the tip-end side of the second projection 32 with a relatively large projection height.

With the projection height H2 of the second projection 32 continuously increased from the base-end side toward the tip-end side, a projection end portion of the second projection 32 can be kept from being cornered. Thus, the above-described effects can be achieved while keeping canal walls, etc. in the body from being damaged by the second projection 32.

In the configuration where the projection height H2 of the second projection 32 is increased from the base-end side toward the tip-end side of the second projection 32, the width W2 of the second projection 32 is increased from the base-end side toward the tip-end side. In this case, in making a cut in the lesion with the second projection 32, the second projection 32 can be favorably kept from leaning therethroughout in the longitudinal direction.

Alternatively, it is possible that the second projection 32 is kept from leaning by increasing the width of the second projection 32 therethroughout in the longitudinal direction. This case, however, entails a disadvantage such as a decrease in the flexibility of the balloon 13. In this regard, the above-described configuration can achieve the above-described effects while avoiding such a disadvantage.

The present invention is not limited to the above-described embodiment but may be implemented, for example, as follows.

(1) In the above-described embodiment, the projection height H2 of the second projection 32 is continuously increased from the base-end side toward the tip-end side, but the projection height H2 may be gradually increased from the base-end side toward the tip-end side. For example, it is possible that the projection height H2 on the base-end side of the second projection 32 is the same as the projection height H1 of the first projection 31 while the projection height H2 on the tip-end side of the second projection 32 is set at a predetermined height larger than the projection height H1 of the first projection 31. It should be noted that in this case, the above-described tip-end side of the second projection 32 corresponds to a "high projection".

Further, the projection height H2 of the second projection 32 is not necessarily increased from the base-end side toward the tip-end side and, for example, the projection height H2 of the second projection 32 may be the same dimension (however, a dimension larger than the projection height H1) throughout the second projection 32 in the longitudinal direction.

(2) In the above-described embodiment, the width W2 of the second projection 32 is continuously increased from the base-end side toward the tip-end side, but the width W2 may be gradually increased from the base-end side toward the tip-end side. Further, the width W2 of the second projection 32 is not necessarily increased from the base-end side toward the tip-end side and, for example, the width W2 may be the same dimension throughout the second projection 32 in the longitudinal direction.

(3) In the above-described embodiment, the first projection 31, the second projection 32, and the third projection 33 are provided continuously in the axial direction, but these projections 31 to 33 may be discontinuous with each other. For example, it is possible that the second projection 32 and the third projection 33 are offset in the circumferential direction of the balloon 13 with respect to the first projection 31.

(4) In the case where the projections 31 to 33 are discontinuous, at least one of these projections 31 to 33 may be provided such that it extends in a direction different from the axial direction along the outer surface of the balloon 13. For example, it may be provided such that it extends in the circumferential direction of the balloon 13.

(5) In the above-described embodiment, the linear projection 30 is integrated with the balloon 13, but a linear projection (hereinafter, referred to as a linear member) may be formed independent of the balloon 13. In this case, for example, it is possible that the linear member is formed of a resin material with elasticity and provided such that it straddles the balloon 13 in the axial direction on the outer circumferential side of the balloon 13. In this case, it is possible that the linear member is bonded to the outer tube 15 at a base-end portion thereof while bonded to a tip-end portion of the inner tube 16 at a tip-end portion thereof.

In such a configuration, the linear member is provided such that it extends in the axial direction on the outer surface of the balloon 13 when the balloon 13 is inflated. In this case, with the linear member projectingly provided on the outer surface of the balloon 13, such a configuration also enables a cut to be made in a lesion with the linear member when the balloon 13 is inflated, so that the lesion can be broken with the cut serving as a trigger.

In this connection, the above-described linear member is provided such that it straddles the straight tube region 13c and the cone regions 13b and 13d when the balloon 13 is inflated. Accordingly, the linear member includes a first linear portion provided on the straight tube region 13c, a second linear portion provided on the tip-end cone region 13d, and a third linear portion provided on the base-end cone region 13b. In this case, it is possible that the linear member is formed such that a projection height of the second linear portion from the outer surface of the balloon 13 is larger than a projection height of the first linear portion. In a case where a lesion is large, this makes it possible to, in inflating the balloon 13 with the tip-end cone region 13d introduced inside the lesion, easily make a cut in the lesion with the second linear portion on the region 13d. Thus, in the case where a lesion is large, the lesion can be favorably broken as in the above-described embodiment. It should be noted that in the above-described example, the first linear portion corresponds to a first projection and the second linear portion corresponds to a second projection.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

10 . . . balloon catheter, 13 . . . balloon, 13c . . . straight tube region as straight tube portion, 13d . . . tip-end cone region as tip-end tapered portion, 30 . . . linear projection, 31 . . . first projection, 32 . . . second projection

What is claimed is:

1. A balloon catheter comprising:
an inflatable balloon disposed on a tip-end side of the balloon catheter, wherein the balloon comprises:
an inflatable straight tube portion; and
a tip-end side tapered portion tapered from a tip end of the straight tube portion toward the tip-end side; and
projections that project from an outer surface of the balloon and linearly extend along the outer surface, wherein the projections include:
a first projection disposed at the straight tube portion; and
a second projection disposed at the tip-end side tapered portion, wherein at least a part of the second projection in a longitudinal direction of the second projection has a height larger than a height of the first projection, and
a base of the second projection has a width larger than a width of a base of the first projection.

2. The balloon catheter according to claim 1, wherein
the second projection extends in an axial direction of the balloon along an outer surface of the tip-end side tapered portion, and
the height of the second projection becomes larger from a base-end side of the balloon catheter toward the tip-end side such that the second projection is disposed at least on the tip-end side.

3. The balloon catheter according to claim 2, wherein the height of the second projection continuously becomes larger from the base-end side toward the tip-end side.

4. The balloon catheter according to claim 2, wherein a width of the second projection becomes larger from the base-end side toward the tip-end side.

5. The balloon catheter according to claim 3, wherein a width of the second projection becomes larger from the base-end side toward the tip-end side.

* * * * *